(12) United States Patent
Shoenfeld

(10) Patent No.: US 7,734,372 B2
(45) Date of Patent: Jun. 8, 2010

(54) WALL MOUNTED MEDICATIONS CABINET AND SYSTEM

(75) Inventor: Norman A. Shoenfeld, Livingston, NJ (US)

(73) Assignee: S&S X-Ray Products, Inc., Pen Argyl, PA (US)

( * ) Notice: Subject to any disclaimer, the term of this patent is extended or adjusted under 35 U.S.C. 154(b) by 0 days.

(21) Appl. No.: 12/399,414

(22) Filed: Mar. 6, 2009

(65) Prior Publication Data

US 2009/0159608 A1 Jun. 25, 2009

Related U.S. Application Data

(62) Division of application No. 11/403,064, filed on Apr. 12, 2006, now Pat. No. 7,668,620.

(51) Int. Cl.
*G06F 17/00* (2006.01)
(52) U.S. Cl. ........................ 700/237; 700/231; 700/232; 700/244
(58) Field of Classification Search ................. 700/231, 700/232, 236, 237, 244
See application file for complete search history.

(56) References Cited

U.S. PATENT DOCUMENTS

| | | | | |
|---|---|---|---|---|
| 3,762,601 | A | * | 10/1973 | McLaughlin ................... 221/2 |
| 5,905,653 | A | * | 5/1999 | Higham et al. .............. 700/244 |
| 5,940,306 | A | * | 8/1999 | Gardner et al. .............. 700/244 |
| 6,003,008 | A | * | 12/1999 | Postrel et al. ................... 705/4 |
| 6,065,819 | A | * | 5/2000 | Holmes et al. .............. 312/215 |
| 6,636,780 | B1 | * | 10/2003 | Haitin et al. ................ 700/236 |
| 6,735,497 | B2 | * | 5/2004 | Wallace et al. .............. 700/231 |
| 6,810,833 | B2 | * | 11/2004 | Bonner et al. ............... 119/455 |
| 2003/0117281 | A1 | * | 6/2003 | Sriharto et al. ........... 340/568.1 |
| 2003/0222548 | A1 | * | 12/2003 | Richardson et al. ......... 312/209 |
| 2007/0244598 | A1 | * | 10/2007 | Shoenfeld .................. 700/236 |

* cited by examiner

*Primary Examiner*—Gene Crawford
*Assistant Examiner*—Michael K Collins
(74) *Attorney, Agent, or Firm*—Bernhard P. Molldrem, Jr.

(57) ABSTRACT

A wall-mounted medications cabinet has at least one, and preferably up to four locking drawers, each with a removable bin holding the medications for a given patient. The drawers are each independently openable electronically. This can be accomplished using an incorporated PC with a touch screen monitor, or authorized access can be obtained via a network. The cabinet may be connected using USB or ethernet interface. A key lock can provide access in the event of a power failure.

6 Claims, 3 Drawing Sheets

WALL MOUNTED MEDICATIONS CABINET AND SYSTEM

This is a Division of my U.S. patent application Ser. No. 11/403,064, filed Apr. 12, 2006, now U.S. Pat. No. 7,668,620.

BACKGROUND OF THE INVENTION

This invention relates to cabinets or storage facilities for keeping supply articles, and is more particularly directed to a system to modernize supply chain management and track inventory items. The invention is more specifically directed to a cabinet suitable for use in a hospital or health care facility, for providing controlled access to a stock of supply items such as dressings, tape, IV bags, infusion kits, gloves, masks, tissues, and personal items, and more specifically to a controlled access cabinet that facilitates keeping an audit trail of access to the various supply items stored in the cabinet.

In general, pharmaceuticals are delivered to patients when needed, and this typically involves use of a medications cart containing the prescription medications for all the patients on a given floor of the hospital or health care center. This means that the cart is typically loaded in a pharmacy department and then is brought to the particular hospital floor. The cart is wheeled from room to room to deliver each patient his or her drugs at the time that the nurse or other practitioner is to administer them. The use of a cart has been more convenient and more efficient than obtaining each patient's medications individually. However, the current system of using a cart to transport medications room to room is inefficient and awkward. Typically, the nurse has to push or pull the cart, and the cart, being bulky and heavy (typically 125 pounds) can be unwieldy where the floors are out of level or where there is carpet. The medications cart is large and obtrusive, and takes up valuable space in the hallway and corridors. Administration of drugs from the cart involves bending and stooping to obtain the drugs from lower drawers. If the nurse needs a particular drug for one of her patients when another nurse has the cart for her medication rounds, then the first nurse has to spend time hunting the cart down and often it is difficult to find the cart. Also, when the pharmacy staff comes to the floor to restock the cart, the cart is often in use and difficult to find, resulting in wasted time for the pharmacy staff. Often, the cart does not fit into the patient's room. In addition, the portable cart requires periodic charging of its batteries, and this task is often overlooked and forgotten until a failure occurs.

It is more convenient and better use of the nurse's time and efforts to keep the pharmaceuticals at the patient locations, i.e., in the patient's room or ward, or in the cluster of rooms where the patient is located. These medications need to be secured, that is, kept locked with a key lock or other mechanism, with access limited only to persons in the nursing staff and pharmacy staff. A record of access to the pharmaceuticals needs to be maintained, but this currently requires making pen-and-ink entries on a paper record, or separately keying in information on separate computer work station.

It would be desirable to employ pharmacy cabinet at the patient location in which medications that have been prescribed for a patient can be loaded by pharmacy staff and stored securely until administered to the patient, which will automatically keep track of access to the cabinet, and which can be accessed by the nurse staff electronically (e.g., using a passcode, a barcode reader, RFID device, fingerprint scanner or wireless means). It is also desirable to ensure that the medications cabinet is kept secure, and with means to ensure that its drawers are closed and locked after each use. However, no measure exists, up to the present, to carry this out.

The state of art of a portable medications cart can be seen with reference to Shoenfeld U.S. Pat. No. 6,775,591, in which the medications cart can be either a wheeled cabinet or a stationary hallway device.

OBJECTS AND SUMMARY OF THE INVENTION

Accordingly, it is an object of the present invention to provide a medications cabinet with secure locking arrangement that avoids the drawbacks of the prior art.

It is another object to provide a medications cabinet and keeps track of the identity or persons accessing the cabinet and times of such access, for each of a number of similar medications cabinets throughout a facility.

It is still another object to provide a medication cabinet that is adapted to be mounted on a wall of a patient room or in some cases a wall at a convenient location in a cluster of patient rooms. The medications cabinet has an enclosure with a front wall and at least one side wall. There are one or more locking drawers in the enclosure, with each drawer including a medications bin that can be pulled out after access is granted to an authorized person, e.g., a nurse. The medications bins each have a proximal end that is disposed at the side wall of the cabinet when the bin is in a closed position. The distal end of the bin is situated within the enclosure. Each drawer has a slide mechanism that permits the medications bin to be pulled out to an open position to allow access to the bin and then to be pushed back in to its closed position. For each drawer there is a releasable latch mechanism inside the enclosure that engages a member that is affixed onto the associated medications bin when the latter is in its closed position. The latch mechanism serves to lock the drawer, but is movable between its locked position and an unlocked position. In the latter position, the latch means releases the associated latching member on the medications bin to release or unlock it.

The cabinet also comprises a microprocessor or computer based automatic access facility, such that a nurse or other authorized person to actuate the releasable latch mechanism (for a given patient's medications drawer) to its unlocked condition so the nurse can access that drawer. The automatic access facility then returns said latch mechanism to its locked position to secure the drawer bin when returned to its closed position.

In one favorable implementation, the latch mechanism can have a latch member that is pivotally supported on a horizontal pivot, and associated latching member on the bin can be formed of a transverse strike plate formed on the distal end of the bin.

In an embodiment of the medications cabinet, the latch member is a bar or lever with a hook member formed at its end and with a slanting surface that engages the transverse strike plate to rise over it and with a blocking surface that engages behind the strike plate to hold the bin against being pulled out. The latch mechanism can further include a servo motor associated with the latch member for lifting same from its locked to its unlocked position.

In some embodiments, the cabinet may have only a single drawer, but in others there can be two, three, or more medications drawers. Where the cabinet has a plurality of drawers, these may be superposed one above another. Each drawer has its own respective latch mechanism, and said latch mechanisms are each independently actuable. The automatic access facility of the medications cabinet ensures that only one of the drawers is unlocked and opened at a time.

Each of the bins can be removed and replaced, so that the pharmacy staff can restock the medications cabinet by replacing the entire bin of the medications drawer. These can be plastic 5-inch medical cart drawer bins, as discussed in my U.S. Pat. No. 6,775,591. This simplifies and speeds the pharmacy operation and also eliminates a source of possible errors.

The cabinet may employ a touch screen computer monitor mounted, e.g., in a VESA mount incorporated into the front wall of the cabinet enclosure to serve as automatic access facility. The nurse or other authorized person can enter a pass code and identification onto soft keys on the touch screen, or through other means such as a card swipe card reader, an RFID receiver, fingerprint scanner or other similar means for identifying the care giver for access. The touch screen computer monitor may be part of a PC computer or may connect with a unit inside the cabinet. Alternatively, the cabinet may have a small touchscreen display. The PC may employ a network interface for connecting with a hospital computer network, so that the locked drawers can be opened remotely via the hospital computer network. Also the touch screen computer can include DVD player means for providing visual program material to a patient. This may be for patient entertainment purposes, or it may be used for providing educational or instructional material concerning therapy for that patient. The video material can also be supplied to each individual cabinet computer via the hospital network, and each can have different independent material. Access to the cabinet drawers can be achieved using a wireless hand-held device, e.g., a wireless Palm Pilot. This can employ Wi-Fi, infrared, or blue tooth technology.

Each medications drawer may have a sensor coupled directly or indirectly to the touch screen computer or automatic access provision detecting if the drawer bin is in its closed position. If the drawer has been left open for more than some programmed threshold time, a local alarm, i.e., buzzer, can be sounded, and the open status is also transmitted to the main hospital computer. As aforesaid, automatic access can be gained, using a network interface and cable (either wire or wireless) connecting the network interface to the hospital computer network. This may involve a USB interface. The drawers can be opened electronically using a USB or ethernet cable (or similar serial cable device). Software, which may be installed in the cabinet on-board computer, the remote computer system, or both, keeps an audit trail of when each cabinet was opened, and who opened it. The same software and network can control multiple locks on different cabinets throughout a facility, i.e., nursing home, hospital, or other health care facility. The software may also provide an audit trail for remotely unlocked refrigerators in which some medications are stored.

The medications cabinet may additionally have a key lock cylinder mechanism for emergency access to the medications in the drawers, e.g., for access in the event of power failure or computer outage.

The remote hospital computer system can includes software assigning a respective serial number code to each individual medications cabinet, permitting the remote computer system to lock and unlock independently each of a plurality of door locks similarly connected with the hospital computer system.

The pharmacy staff can distribute the various patient prescription orders at convenient times, e.g., during non-busy hours, supplying a replacement patient bin in the cabinet, and removing the empty bin to return to the pharmacy. At the same time, the pharmacy staff can deposit the temperature sensitive medications into the patient refrigerator. Then the medications are ready for the nurse or other care giver to administer on schedule, without having to bring a cart from room to room.

Similar cabinets may be used in the various laboratories or clinics for controlled storage of items, where access needs to be limited, and it is desirable to create an audit trail.

There are several clear advantages that attend the wall mounted cabinet of this invention: As the unit is mounted in the wall in the patient room, there is no heavy cart to push around. Patient-specific medications are always in the patient room, not in a cart which may be somewhere far down the hall. Pharmacy can restock the patient medication drawers without having to hunt for the cart. The cabinet remains in the same place from each day to the next. The nurse spends less time in the hallway, and more time in the room with the patient. With much less professional time being spent in the hallway with the cart, the nurse and doctor spend more time with the patient. More professional time spent in the patient room translates into more time being spent checking on the patient. The wall mounted dispensing cabinet brings the electronic record keeping right to the patient's bedside. There is more accurate record keeping, and the audit trail notes each time a nurse is actually present in the room at the time of medication dispensing.

The above and many other objects, features, and advantages of this invention will become apparent from the ensuing description of a selected preferred embodiment, which is to be considered in connection with the accompanying Drawing.

DETAILED DESCRIPTION OF THE PREFERRED EMBODIMENT

Figure 1:
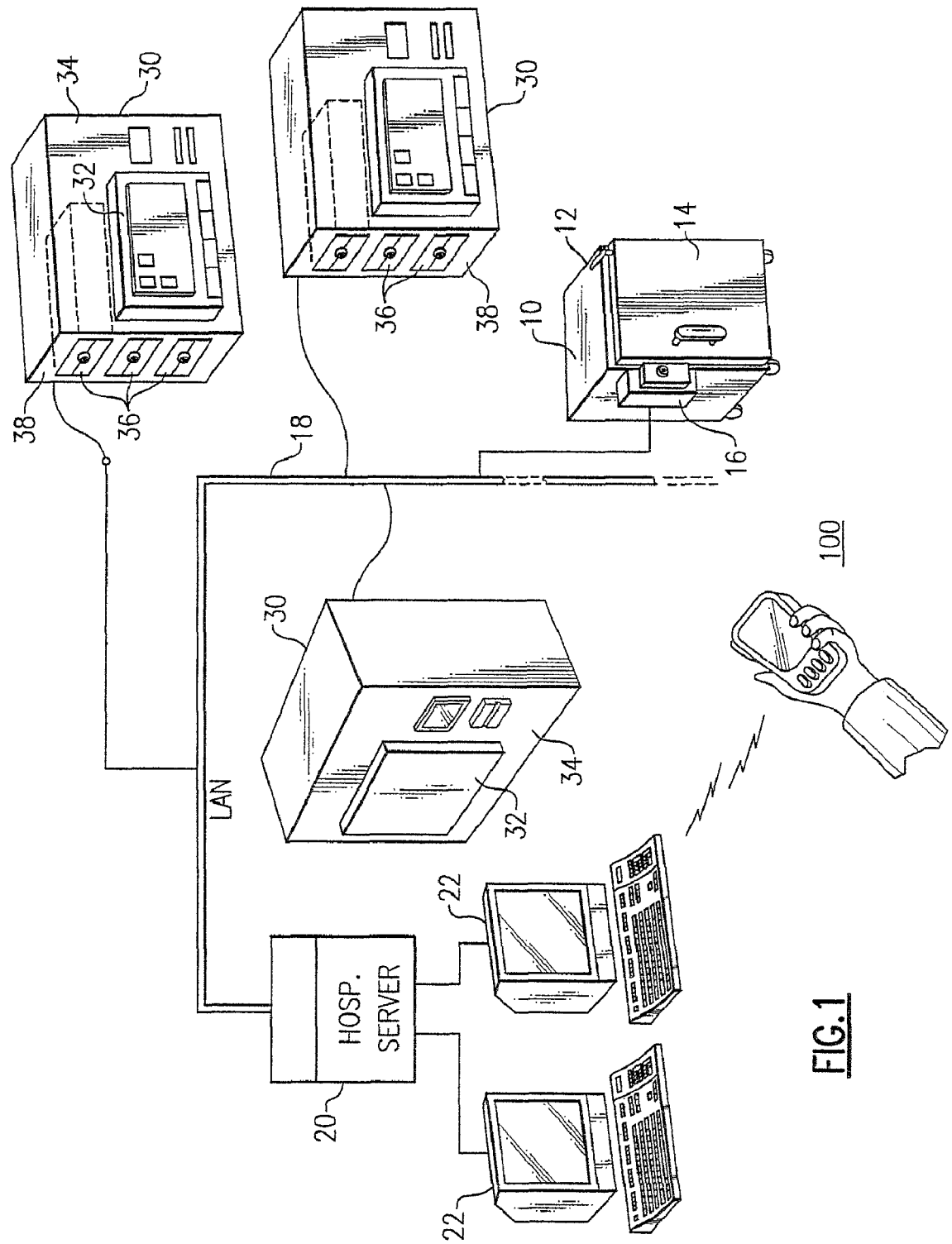
FIG. 1 is a schematic view of a network-connected system including medication storage cabinet(s) according to one preferred embodiment of this invention.
Figure 2:
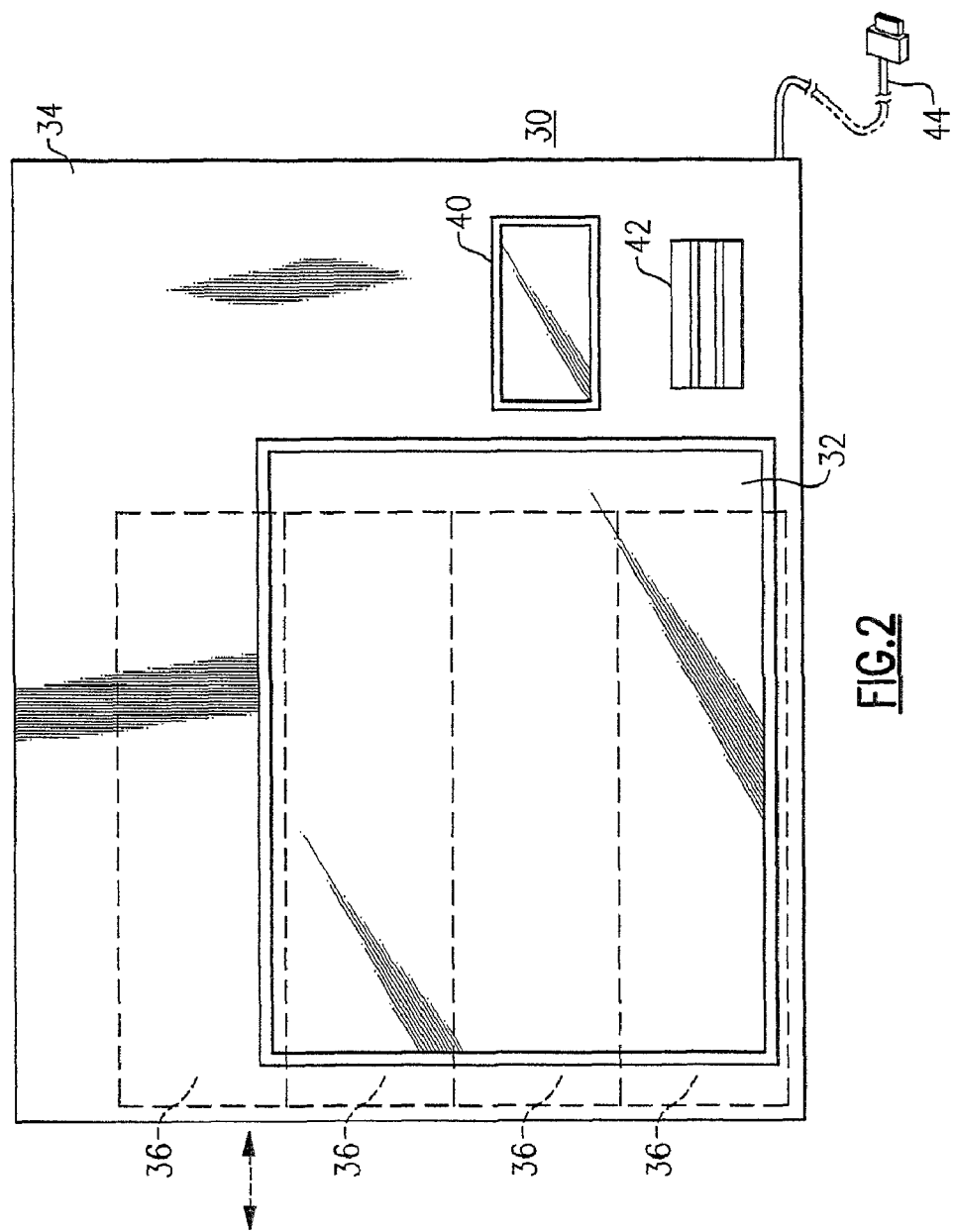
FIG. 2 is a front view of the medication cabinet of this embodiment.
Figure 4:
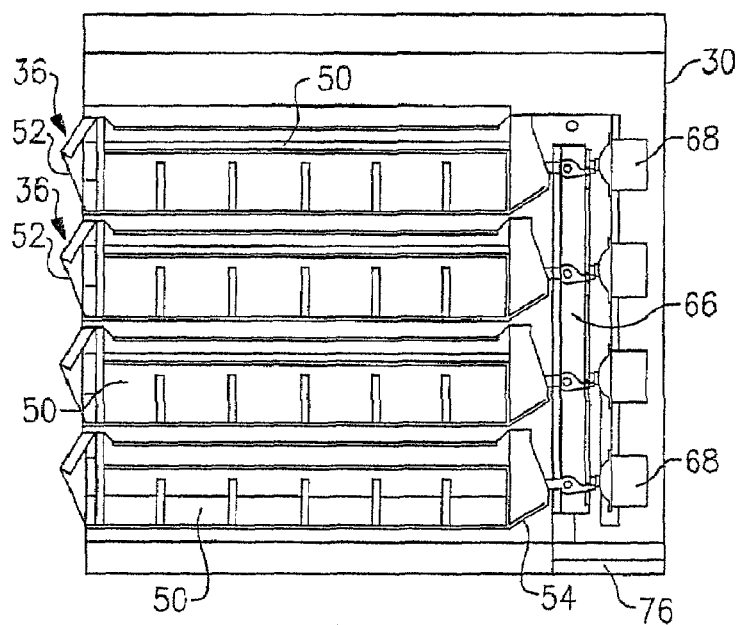
FIGS. 4, 5, and 6 are detailed sectional front elevation, side elevation and top plan view, respectively.
Figure 5:
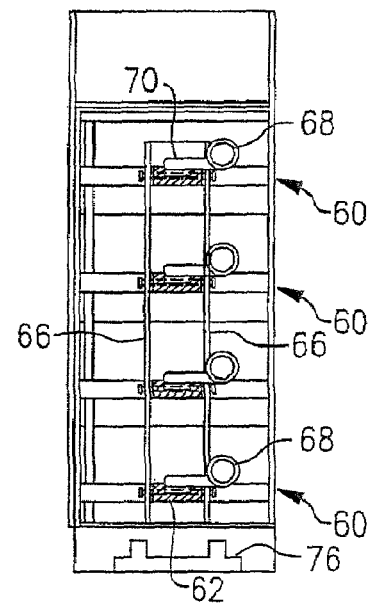
Figure 6:
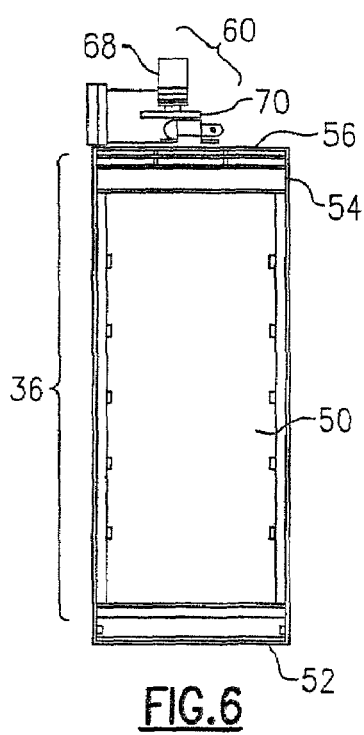

With reference to the Drawing, and initially to FIGS. 1 and 2, a medication dispensing arrangement in a hospital or other health care facility can employ one or more small refrigerators 10 in the patient rooms (or at the hubs of clusters of patient rooms) for storage and controlled access to medications and pharmaceuticals that need to be kept refrigerated. The refrigerator 10 has a cabinet body 12 and a door 14 that closes over the front of the cabinet body. In the illustrated embodiment, the door 14 is hinged at the right and opens from the left, but the refrigerator could as easily be a right-opening version. Typically, the door and cabinet have a magnetic closure of sufficient strength to maintain compression on the door seal. In this embodiment, the refrigerator has attached onto it a remote actuation door lock assembly 16, as described in more detail in my copending patent application Ser. No. 11/391,986, filed Mar. 29, 2006. The door lock assembly is connected electrically or electronically via a network 18, e.g., a LAN, that makes either a wired or wireless connection with a hospital computer server 20, to which one or more work station computers 22, 22 are connected. The LAN 18 can also connect with door lock assemblies for additional med storage refrigerators. These may be located in other patient rooms or in other locations throughout the facility.

Also shown here is a wall mounted medications cabinet 30 that embodies an aspect of this invention. The cabinet 30 may be mounted on the wall of the patient room, and also is or may be coupled electronically with the hospital LAN 22. The purpose of the wall mounted cabinet 30 is to provide controlled access in the patient's room to normal prescriptive medications in one of several (here, three or four) computer locked drawers 36.

In this embodiment, the wall-mounted medications cabinet 30 has an enclosure or housing, with an associated touch-screen computer 32 mounted on a front wall or panel 34. The touch-screen computer serves as a facility on which nurse or other authorized health care provider can enter an authorization code to achieve access to a patient's medications that are stored in one of the pull-out cabinet drawer(s) 36, which open at a side wall 38 of the cabinet, here the left wall. The same touch screen computer 32 may be used via the LAN 18 to release the lock mechanism on an refrigerator lock. Alternatively, the health care provider may employ a wireless hand-held device 100 that communicates with one of the computer work stations 22 to access the patient's medications drawer 36.

In an alternative embodiment, e.g., in a physician's office, the wall mounted cabinet 30 may be free standing, and may be used for controlled access to certain items. The on-board computer 32 contains programming and memory to keep an audit trail of the times of opening and closing of each drawer and the person accessing the drawer.

Figure 3:
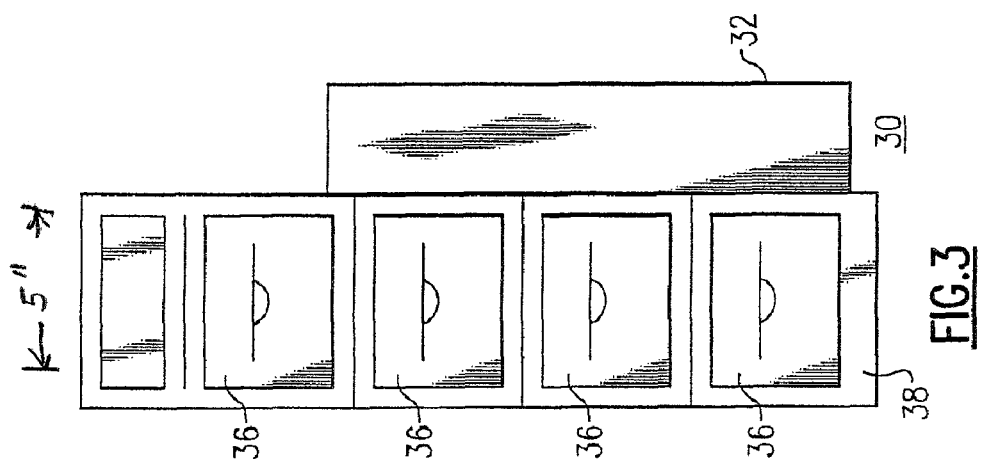
FIG. 3 is a side view of this embodiment

With reference now to FIGS. 2 and 3, the touch-screen computer 32 is shown as having an active screen monitor and a thin CPU or PC mounted directly behind it on the front wall 34. This PC contains the electronics, memory drives, and interfaces to operate the cabinet. The medication drawers have a proximal or front end located at the left side wall 38, and with the distal ends situated within the cabinet, to engage a locking or latching mechanism to be described shortly. Each drawer has an elongated tray or bin, and a slide mechanism permitting the tray to be pulled out and removed. The construction can be similar to that described in connection with my earlier U.S. Pat. No. 6,775,571.

To the right of the touch screen 32 is an LCD display 40 and a card reader or badge reader 42. The latter can be a bar-code reader, magnetic stripe reader, configured as a card-swipe mechanism, or may employ an RFID reader, smart-card reader, or fingerprint scanner.

The cabinet 30 also has a USB cable 44, or alternatively an ethernet cable or equivalent connection, extending from a USB interface, ethernet interface, or the like within the cabinet. This connection is employed to connect, either by wire or wirelessly, with the computer network or LAN 18.

Now with reference to FIGS. 4, 5, 6 and 7, each of the drawer has a removable bin or tray 50, which can be made of a suitable durable plastic material, with each drawer having a pull handle 52 formed at its proximal end (i.e., left as shown) and a latching structure 54 formed at its distal end (i.e., to the right in these drawing views). The latching structure includes a latching plate or strike plate 56, that lies in a generally vertical plane and extends transversely across the distal end of the bin 50.

For each drawer 36 there is an associated latch mechanism 60 mounted within the cabinet. Each latch mechanism employs a latch lever or bar 62 that is mounted on a transverse pivot pin 64, with the pivot pins for the four drawers being supported one above the other on a pair of vertical rails 66, 66.

Figure 7:
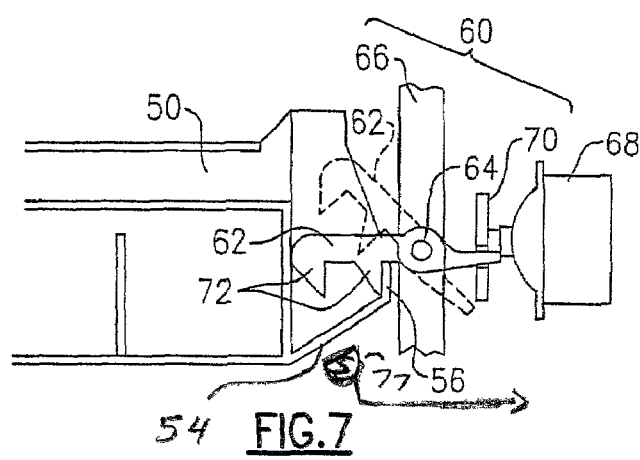
FIG. 7 is partial side view showing the latch mechanism of this embodiment.

The latch lever 62 has a normal locked position, as shown in solid line in FIG. 7, and a lifted or raised release position as shown in dashed lines. A servo motor and drive 68 are actuated for lifting the latch lever 62 and unlocking or releasing the associated drawer. The servo drive includes a rotary mechanism, e.g., a bar 70 that swings down to push against a nose of the latch lever. The latch lever 62 has a pair of slant teeth 72, with each tooth having slanting nose surface at its distal side (left in the drawing), and a recess behind this for securing the latch strike plate 46 in the drawer bin or tray 50. The slanting nose surface allows the lever to lift and then drops to latch and capture the strike plate when the drawer is pushed closed.

A circuit board 76, here positioned below the drawer latch mechanisms, can be controlled by the computer 32 (or by the card reader or other devices) to provide drive current to the servo motors 68 when the authorized person is granted access to the medications drawer. An interface device, for either the USB or ethernet cable, may be located on the circuit board 76. A serial-ethernet bridge interface may be used here. The host computer, e.g. hospital server 20, may use a Window, UNIX, LINUX or other suitable system. The system can employ a card reader, e.g., bar code or magnetic stripe, RFID, smart-card reader, or fingerprint scanner to provide access and unlock the respective medications drawer, in which case access may be by means of a card or badge carried by the health care provider.

The power for the computer 32 and for the latching mechanism in the cabinet 30 may be provided by local AC power, by DC power over the network connection or otherwise, and backup batteries may favorably be included so that access to the medications drawers is possible during a power or computer network failure.

A magnetic or mechanical proximity sensor 77 may be situated at or near the distal or inner end 54 of each tray or bin 50, and is coupled to the circuit board 76 to provide an indication of the open/closed status of each drawer 36. This status can then be communicated via the cable 44 and LAN 18 to the hospital computer system. The system can be programmed to alert the pharmacy personnel if one of the drawers in any of the cabinets has been left open for longer than a pre-selected programmed time limit. Also, while not shown here, the cabinet 30 may have one or more LED lock/unlock status indicators. There may be one indicator for each drawer 36. These may be adapted to glow red when the drawer is locked, and to glow green when the particular medications drawer is unlocked. A no-glow or dark indication then indicates a fault or possible system failure. Flashing on-off intermittently can be used to indicate an emergency condition.

An audible sounder may be incorporated within the cabinet enclosure which emits a tone or buzz if one of the medications drawers remains open for a time that exceeds the programmed time limit. The sounder alerts the nurse or other authorized attendant to close the medications drawer, if the drawer has been inadvertently left open.

While not shown here in detail, the cabinet can favorably be provided with a key lock cylinder which can be rotated for mechanically lifting one or all of the latch levers 62. This arrangement permits authorized personnel to open the cabinet 30 manually (with a key) in the event a power failure, network outage, or other event that might preclude obtaining electronic access.

In a preferred embodiment, the hospital computer system keeps track of the times each medications drawer is unlocked, and the of identities of authorized personnel who obtain (or attempt to obtain) access, i.e., the system creates an audit trail of health providers who request access.

While the invention has been described hereinabove with reference to selected preferred embodiments, it should be recognized that the invention is not limited to those precise embodiments. Rather, many modification and variations would present themselves to persons skilled in the art without departing from the scope and spirit of this invention, as defined in the appended claims.

I claim:

1. A method of dispensing medication when needed to patients in respective patient rooms at a health care facility in which medications are kept at a pharmacy and when needed are brought to respective patient rooms within the facility, comprising:
   a. providing each of said patient rooms with a medications cabinet, and mounting each said cabinet upon a wall of the respective patient room, wherein each said medications cabinet includes
      an enclosure that is adapted to be mounted on a wall of a patient room and supported at an elevated position above a floor of the room, the enclosure having a back adapted to be affixed to said wall of the patient room, a front wall, a bottom wall, a left side wall and a right side wall;
      one or more locking drawers in said enclosure, each drawer being adapted to hold patient-specific medication for the respective patient in the room, the one or more drawers each having a proximal-distal axis extending along a lateral axis defined between said left and right side walls, and each said drawer including
         an elongated slide-out removeable medications bin having an open top permitting access to contents of the bin only when the drawer is pulled out to an open position, and having a proximal end disposed, when said bin is in a closed position, at one of said left and right side walls and a distal end situated within said enclosure;
         respective slide means supporting each said bin when the latter is in its open position and in its closed position, and permitting the bin to be pulled out laterally along its proximal-distal axis to an open position to allow access to the bin and permitting the bin to be pushed back in to its closed position; and
         respective releasable latch means within said enclosure for releasably engaging a respective member on each said bin in its closed position to lock the drawer, and being movable between a locked position and an unlocked position in which the latch means releases said member; and
      for each said drawer a proximity sensor positioned at or near a distal portion of the associated drawer to detect if the drawer is pushed back in to its closed position and to indicate an open/closed status of the associated drawer; and
      automatic access means permitting an authorized person to actuate the releasable latch means to its unlocked condition to permit access to said drawer and automatically returning said latch means to its locked position to secure the drawer bin when pushed in and returned to its closed position, wherein the access means is operable to actuate said latch means open only if each said proximity sensor detects that its respective drawer is in its closed position;
   b. filling a plurality of said medications bins at said pharmacy with the medications for the respective patients in said patient rooms;
   c. bringing said medications bins from the pharmacy to the respective patient rooms;
   d. loading each said medications bin into an associated one of the locking drawers of the medications cabinet in the associated patient room;
   e. providing an authorized health care professional with means to achieve access to the drawers in the respective cabinet;
   f. accessing said drawers in said medications cabinets to provide the medications therein to the associated patient in the patient room; and
   g. replacing said bin in the drawer and securing the drawer to its closed position.

2. The method of claim 1, wherein said automatic access means includes a touch-screen computer mounted on a front wall of the cabinet enclosure, and said authorized medical professional achieves access by entering an access code into said touch-screen computer.

3. The method of claim 2, further comprising providing patient instructive video material concerning therapy for the associated patient, and playing said video material on said touch-screen computer.

4. The method of claim 1, further comprising automatically creating an audit trail for each said medications cabinet of the access history for each said cabinet, including the time or each respective access and the identity of the person attempting such access.

5. The method of claim 1, wherein said step of loading includes lifting out a previously emptied medication bin in the associated locking drawer and replacing it with the medications bin brought from the pharmacy.

6. The method of claim 1, said automatic access means permitting the drawer to be released only when each said bin is in its closed position.

* * * * *